United States Patent [19]
Green

[11] Patent Number: 4,652,667
[45] Date of Patent: Mar. 24, 1987

[54] PROCESS FOR TRANSESTERIFICATION OF CARBONATE ESTERS AND CARBOXYLIC ACID ESTERS USING A CYCLIC AMIDINE CATALYST

[75] Inventor: Michael J. Green, Hull, England

[73] Assignee: BP Chemicals Limited, London, England

[21] Appl. No.: 692,678

[22] Filed: Jan. 18, 1985

[30] Foreign Application Priority Data

Jan. 25, 1984 [GB] United Kingdom ................. 8401919

[51] Int. Cl.$^4$ ...................... C07C 68/06; C07C 67/02
[52] U.S. Cl. .................................... 558/277; 549/230; 560/217; 560/234
[58] Field of Search ............................ 260/463, 243.3; 549/228, 229, 230; 564/230; 544/279, 282; 560/103, 217, 234; 558/277

[56] References Cited

U.S. PATENT DOCUMENTS 4,358,613 11/1982 Mark .................................... 564/230
4,435,331 3/1984 Licciardello et al. .............. 260/463

FOREIGN PATENT DOCUMENTS 0110629 6/1984 European Pat. Off. .
2615665 10/1976 Fed. Rep. of Germany ...... 260/463
2749754 5/1979 Fed. Rep. of Germany ...... 260/463
955232 4/1964 United Kingdom ................ 260/463
1489736 10/1977 United Kingdom ................ 260/463

Primary Examiner—Donald G. Daus
Assistant Examiner—Stephen M. Kapner
Attorney, Agent, or Firm—Brooks, Haidt, Haffner & Delahunty

[57] ABSTRACT

A process is provided for the transesterification of carbonate esters and carboxylic acid esters at elevated temperatures and in the presence of an effective amount of an amidine compound.

10 Claims, No Drawings

PROCESS FOR TRANSESTERIFICATION OF CARBONATE ESTERS AND CARBOXYLIC ACID ESTERS USING A CYCLIC AMIDINE CATALYST

The present invention relates to the transesterification of carbonate esters and carboxylic acid esters by contacting a carbonate ester and a carboxylic acid ester in the presence of an amidine compound as catalyst.

GB No. 1,489,736 discloses a method for the transesterification of a carbonate ester and an alcohol in the presence of a Lewis base catalyst.

It has now been found that carbonate esters and carboxylic acid esters can be transesterified by reacting a carbonate ester and a first carboxylic acid ester in the presence of, as catalyst, an effective amount of an amidine compound.

Accordingly, the present invention provides a process for the transesterification of carbonate esters and carboxylic acid esters comprising contacting at elevated temperature a carbonate ester with a carboxylic acid ester in the presence of an effective amount of an amidine compound.

The carboxylic acid ester used as the reactant herein can be any carboxylic acid ester, but is preferably an ester of a $C_1$ to $C_{20}$ aliphatic carboxylic acid. The ester group (the substituent attached to the oxygen atom) within the carboxylic acid ester is preferably a substituted or unsubstituted short chain aliphatic hydrocarbyl radical such as a $C_1$ to $C_{10}$ alkyl, a $C_2$ to $C_{10}$ alkenyl and the like. Preferred carboxylic acid esters include methyl acetate, ethyl acetate and methyl propionate.

The carbonate ester which is used as co-reactant with the carboxylic acid ester can be any carbonate ester, but is preferably an alkylene carbonate having the general formula:

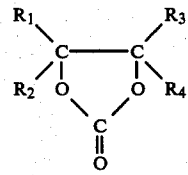

wherein each of $R_1$, $R_2$, $R_3$ and $R_4$ are independently a hydrogen atom or a hydrocarbyl radical. Typical hydrocarbyl radicals include substituted or unsubstituted $C_1$ to $C_{10}$ alkyls and $C_2$ to $C_{10}$ alkenyls. Preferred examples of suitable alkylene carbonates are ethylene carbonate, propylene carbonate and butylene carbonate.

By transesterification is meant a reaction in which the ester group on the carboxylic acid ester (i.e. $R^3$) displaces one or both ester groups on the carbonate ester with the corresponding transfer of the ester groups from the carbonate ester to the carboxylic acid ester. For example, one embodiment of the transesterification processes of the present invention can be illustrated by the following reaction scheme:

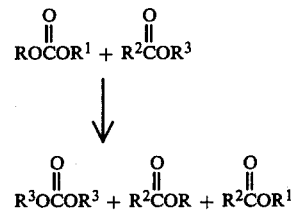

Alternatively, only one of the ester groups on the carbonate ester can be transesterified rather than both ester groups as illustrated above.

It will be obvious to one skilled in the art that the carbonate ester and carboxylic acid ester which constitute the products of the inventive process will depend on the particular carbonate ester and carboxylic acid ester reactants. In the case where an alkylene carbonate ester and a carboxylic acid alkyl ester are used as reactants, the transesterified products will be a dialkyl carbonate and a 1,2-alkanediol dicarboxylate.

The catalyst used to carry out the transesterification reaction is an amidine compound in homogeneous or heterogeneous form. By the term amidine compound is meant a compound containing the group

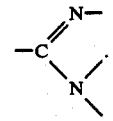

Conveniently, the free valencies on the nitrogen atoms are independently attached to carbon atoms or hydrogen and the free valency on the carbon to another carbon atom or a nitrogen atom. Where the carbon atom is attached to a nitrogen atom, the amidine compound will comprise a guanidine.

Although any compound containing the above amidine group will catalyse the present reaction, the preferred amidine compounds are cyclic amidines. Cyclic amidines are defined as those amidines wherein at least one of the nitrogen atoms is part of an alicyclic or heterocyclic substituted or unsubstituted hydrocarbyl ring. In the case where the amidine is a guanidine, then any two of the three nitrogen atoms may be in the same ring or in different rings. Those nitrogen atoms which are not part of any ring may form part of a substituted or unsubstituted hydrocarbyl group.

Preferred cyclic amidines are those in which the amidine group forms part of a fused ring system containing 5 and 6 membered rings, 6 and 7 membered rings or two 6 membered rings. For example, such preferred cyclic amidines include 1,5-diazabicyclo [4.3.0] non-5-ene, 1,8-diazabicyclo [5.4.0] undec-7-ene and 1,5,7-triazabicyclo [4.4.0] dec-5-ene.

The catalyst used in the present invention can be homogeneous (unsupported) or heterogeneous (supported). In the heterogeneous catalyst, the amidine compound is chemically bonded to an inert support through the bonding of the surface atoms of the support to one or more of the free valences of the amidine group. This can be accomplished either by direct bonding or through an intermediate hydrocarbyl radical which may, in the case of cyclic amidine compounds, constitute part of the ring structure of the amidine compound.

Suitable supports include organic supports such as polymer resins, e.g. polysytrene, polystyrene/divinyl benzene copolymer, polyacrylate, polypropylene and the like or inorganic supports such as silica, alumina, silica/alumina, clay, zirconia, titania, hafnia, carbides, diatomacrous earth, zeolites and the like.

The process of the present invention is conducted in the liquid phase at either atmospheric pressure or autogenous pressure and at an elevated temperature such as 40° C. and above. The preferred temperature range is from 40° to 150° C.

The concentration of catalyst used is such that the amidine compound corresponds to between 0.01 and 10%, preferably 0.1 to 2%, by weight of the total reaction mixture.

When conducting the inventive process, the reactants are preferably fed to the reaction zone in such a way as to generate a mixture in which the carbonate ester to carboxylic acid ester molar ratio is in the range of 10:1 to 1:10, preferably 5:1 to 1:5. The reaction may be carried out in either a batchwise or a continuous manner.

The present invention will now be illustrated by reference to the following Examples. However, the scope of this invention includes equivalent embodiments, variations and modifications

EXAMPLE 1

A 150 ml round-bottom flask, fitted with a thermocouple pocket and a water cooled condenser, was charged with 17.5 g of methyl acetate, 5.0 g of ethylene carbonate and 0.25 g of 1,5,7-triazabicyclo[4.4.0]dec-5-ene (TBD). The contents of the flask were refluxed for 2 hours and then cooled to room temperatrure. Analysis of the product mixture by gas chromatography showed a 24.6% conversion of ethylene carbonate with dimethylcarbonate and 1,2-ethanediol diacetate as the only reaction products.

COMPARATIVE EXAMPLE A

Example 1 was repeated in the absence of TBD. Analysis of the product showed that no conversion had taken place.

COMPARATIVE EXAMPLE B

Example 1 was repeated except the 0.25 g of triethylamine was used in place of TBD. Analysis of the product after 2 hours reflux showed that no conversion had taken place.

Comparative Examples A and B, which are not part of this invention, show that a catalyst is needed for the reaction and that amine Lewis bases which are not amidines will not catalyse the reaction.

EXAMPLE 2

Example 1 was repeated but in the presence of 0.1 g of TBD only. Analysis of the liquid reaction product showed a 24.9% conversion of ethylene carbonate with dimethyl carbonate and 1,2-ethanediol diacetate as the only reaction products.

EXAMPLE 3

Example 1 was repeated except that the reaction was carried out in a sealed Fischer-Porter tube under an initial nitrogen pressure of 60 psi and at 120° C. After 2 hours at this temperature the reaction vessel was cooled and depressurised. Analysis of the liquid product showed a 22.8% conversion of ethylene carbonate with dimethyl carbonate and 1,2-ethanediol diacetate as the only reaction products.

EXAMPLE 4

Example 1 was repeated except that 17.7 g of ethyl acetate was used in place of methyl acetate. Analysis of the product showed a 16.8% conversion of ethylene carbonate with diethyl carbonate and 1,2-ethanediol diacetate as the only reaction products.

EXAMPLE 5

Example 1 was repeated except that 17.5 g of methyl propionate was used in place of methyl acetate. Analysis of the liquid product showed a 45.6% conversion of ethylene carbonate with a 100% selectivity to dimethyl carbonate, a 43% selectivity to 1,2-ethylene glycol dipropionate and a 57% selectivity to diethylene glycol dipropionate. This example shows that esters other than acetates may be used in this process.

EXAMPLE 6

Example 1 was repeated except that 0.25 g of 1,5-diazabicyclo[4.3.0]non-5-ene was used as a catalyst in place of TBD. Analysis of the liquid product showed a 5% conversion of ethylene carbonate with dimethyl carbonate and 1,2-ethanediol diacetate as the only products.

EXAMPLE 7

Example 1 was repeated except that 0.25 g of 1,8-diazabicyclo[5.4.0]undec-7-ene was used as a catalyst in place of TBD. Analysis of the liquid product showed a 4% conversion of ethylene carbonate with dimethyl carbonate and 1,2-ethanediol diacetate as the only products.

Examples 6 and 7 show that amidines other than TBD can be used to catalyse the reaction between an alkylene carbonate and a carboxylic acid ester.

I claim:

1. A process for the transesterification of carbonate esters and carboxylic acid esters comprising contacting at elevated temperatures a carbonate ester and a carboxylic acid ester in the presence of as catalyst an effective amount of a cyclic amidine compound.

2. The process of claim 1 wherein the amidine compound contains the group

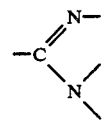

3. The process of claim 1 wherein the cyclic amidine compound is present in concentrations between 0.01% and 10% by weight.

4. The process of claim 1 wherein the cyclic amidine is one in which the amidine group forms part of a fused ring system of a 5 and 6 membered ring, a 6 and 7 member ring or two 6 membered rings.

5. The process of claim 1 wherein the cyclic amidine is 1,5-diazabicyclo [4.3.0 non-5-ene, 1,8-diazabicyclo [5.4.0] undec-7-ene, or 1,5,7-triazabicyclo [4.4.0] dec-5-ene.

6. The process of claim 1 wherein the carboxylic acid ester is an ester of a $C_1$ to $C_{20}$ aliphatic carboxylic acid and the carbonate ester is an alkylene carbonate.

7. The process of claim 6 wherein the carboxylic acid ester contains an ester group which is a $C_1$ to $C_{10}$ alkyl or $C_2$ to $C_{10}$ alkenyl group and the carbonate ester is ethylene carbonate, propylene carbonate or butylene carbonate.

8. The process of claim 1 wherein the carboxylic acid ester is methyl acetate and the carbonate ester is ethylene carbonate.

9. The process of claim 1 wherein the reactants are fed into the reaction zone such that the ratio of carbonate ester to carboxylic acid ester is from 10:1 to 1:10.

10. The process of claim 1 wherein the cyclic amidine compound is a cyclic guanidine.

* * * * *